(12) United States Patent
Turtzo

(10) Patent No.: US 6,254,554 B1
(45) Date of Patent: Jul. 3, 2001

(54) COMPRESSION SLEEVE FOR TREATING LYMPHEDEMA

(75) Inventor: Craig H. Turtzo, Clearwater, FL (US)

(73) Assignee: MEDassist-OP, Inc., Palm Harbor, FL (US)

( * ) Notice: Subject to any disclaimer, the term of this patent is extended or adjusted under 35 U.S.C. 154(b) by 0 days.

(21) Appl. No.: 09/393,726

(22) Filed: Sep. 10, 1999

(51) Int. Cl.⁷ ............................................. A61H 19/00
(52) U.S. Cl. ........................ 601/134; 602/75; 606/201; 606/204
(58) Field of Search ..................... 602/75, 5, 23, 602/27; 606/201, 204; 128/846, 878; 601/134

(56) References Cited

U.S. PATENT DOCUMENTS

| | | |
|---|---|---|
| 4,027,666 | 6/1977 | Marx . |
| 4,469,095 | 9/1984 | Herrera . |
| 4,657,003 * | 4/1987 | Wirtz . |
| 4,832,010 | 5/1989 | Lerman . |
| 5,257,956 | 11/1993 | Ewen . |
| 5,437,621 | 8/1995 | Andrews et al. . |
| 5,449,341 | 9/1995 | Harris . |
| 5,695,452 * | 12/1997 | Grim et al. . |
| 5,735,807 | 4/1998 | Cropper . |
| 5,743,866 | 4/1998 | Bauerfeind et al. . |
| 5,916,183 | 6/1999 | Reid . |

OTHER PUBLICATIONS

Legacy Compression Systems, Aug. 1, 1998 press release.

* cited by examiner

Primary Examiner—Michael A. Brown
Assistant Examiner—Lalita M. Hamilton
(74) Attorney, Agent, or Firm—Greensfelder, Hemker & Gale, P.C.

(57) ABSTRACT

A compression sleeve for treating lymphedema is provided. The compression sleeve is comprised of an outer inelastic fabric layer and an inner flexible sheet padding layer. A plurality of tightening straps are laterally disposed in vertical succession along an exterior side of the sleeve to independently apply circumferential pressure along the length of the sleeve. The sleeve is able to apply a consistent gradient pressure from a distal part of the limb to a proximal end of the limb to help squeeze excess lymph from the limb. The inner padding layer is comprised of a high density foam material provided in a thin, continuous surface, flat sheet and has a high degree of firmness capable of evenly distributing the pressure generated by the tightening straps to prevent pockets of swelling within the sleeve. The compression sleeve can be configured for use with both arms and legs.

37 Claims, 9 Drawing Sheets

COMPRESSION SLEEVE FOR TREATING LYMPHEDEMA

BACKGROUND OF THE INVENTION

The present invention relates to a sleeve apparatus for applying compressive pressure to a person's arm or leg to facilitate the drainage of lymph fluid. An excessive amount of lymphatic fluid can accumulate in one's limb due to trauma to the lymphatic system, creating a condition called lymphedema. This is often seen, for instance, in the case of post-mastectomy patients who have had the lymph system compromised around the treated area. The result is swelling, discomfort, loss of range of motion and activities of daily living. Additionally, the lymph in the affected limb has a very high protein count and can be a potential breeding area for bacteria if the patient's skin is punctured.

There is no viable surgical or pharmacological intervention available to cure lymphedema. The only effective treatment is called Complete Decongestive Physical Therapy ("CDP"). This treatment protocol involves manual lymph massage, bandaging, exercise and education in self-care. The bandaging is intended to create gradient pressure that is highest at the distal area of the limb and which steadily decreases up the limb towards the body. Because it is a goal to drain the limb of all excessive lymph fluid, it is important in the bandaging process to make sure that pockets in the bandages are avoided so that no pools of trapped lymph can be created along the surface of the person's arm.

Self bandaging is time consuming and difficult for the patient to accomplish on his own. There have been several attempts to manufacture a product as a substitute for, or as an adjunct to, self bandaging. Some sleeves comprise an elastic outer shell which snuggly fits against the limb. However, the lymph engorged limb will stretch the outer fabric of the sleeve, therefore defeating its purpose as an effective source of compression. There also exist certain compression sleeves which comprise an inelastic outer sleeve which constrains the swelling of the limb, thus forcing the lymph to drain from the limb back towards the body. Many of these types of devices are intended to be used in conjunction with bandaging wraps and themselves do not provide padding. Needless to say, these types of sleeves can be quite uncomfortable for the patient. There further exists a compression sleeve which provides internal padding having several raised projections. This padding is of a low density type foam and is designed to apply pressure mainly along the points of the projections. The low density foam used in this sleeve is thick and bulky. When worn, it can inhibit flexion of the limb which can lead to discomfort. Further, with this type of sleeve, pooling of lymph fluid can occur at those points in the interstitial area between the raised projections. Accordingly, while lymph flow may be improved, maximum drainage of lymphatic fluid may be precluded. This type of sleeve is useful for prolonged wear, but is not consistent for use with complete decongestive physical therapy where the goal is maximum lymph drainage.

Therefore, there exists the need for a compression sleeve having padding for patient comfort yet having a construction that will aid in providing complete compression to the limb by gradient pressure for maximum drainage of the lymphatic fluid. There further exists the need to provide a compression sleeve that is light in weight and not bulky.

SUMMARY OF THE INVENTION

It is an object of this invention, therefore, to provide a compression sleeve for applying gradient pressure for application to a person's limb in connection with complete decongestive physical therapy to facilitate the drainage of excessive lymphatic fluid from the limb. The compression sleeve of the instant invention is comprised of an inner flexible sheet padding layer and an outer inelastic fabric layer. The inelastic outer layer constricts swelling of the limb which helps promote the flow of lymph out of the limb. A plurality of tightening straps are laterally disposed in vertical succession along an exterior side of the sleeve to independently apply circumferential pressure along the length of the sleeve. This allows the application of a consistent, gradient pressure from a distal part of the limb to its proximal end to help squeeze the excess lymph out of the limb. The inner padding layer is comprised of a high density foam material provided in a thin, continuous surface, flat sheet. The high density foam material comprising the inner padding layer has a high degree of firmness and has a compression factor sufficient to evenly distribute the pressure generated by the circumferential tightening straps. The tightening straps are aligned adjacently in close proximity to each other along the sleeve so that upon application of circumferential pressure by the straps, the padding will not bulge out from between the straps. The inner padding layer is held in place within a pocket formed by a lightweight mesh fabric connected to said inelastic outer layer.

The compression sleeves may be configured for either an arm or a leg. The thin, flat inner foam layer provides less material within the sleeve, thus allowing for a sufficient degree of limb flexion. Further, the sleeve can be formed with a slight angulation approximating the normal degree of limb flexion at rest. As an alternate inner padding layer, a gel sheet may be used. This type of material, while also providing good support, has a high heat flux factor, enabling the patient's limb to remain cool while wearing it on the limb. The gel sheet, with its high heat flux, draws heat from the patient's skin. When the high density foam material is used as an inner padding layer, holes can optionally be placed in the foam so that the patient's skin can breathe and to allow for the release of excess heat.

The leg compression sleeve can be provided with differing density foams bonded or sewn together to help reduce the weight of the sleeve so that it is less likely to slip from the patient's leg due to gravity. Further, one of the foam pads may have a higher degree of rigidity to maintain the elongated sleeve shape.

It is therefore an object of this invention to provide a compression sleeve to facilitate drainage of excessive lymph fluid from a person's limb. It is further an object of this invention to provide such a compression sleeve with a firm, high density foam inner padding layer to evenly distribute the circumferential pressure placed on the limb by the tightening straps. It is still further an object of this invention to provide a compression sleeve having increased breatheability of the inner padding layer as well as a high heat flux factor to increase the patient's comfort.

The above features are objects of this invention. Further objects will appear in the detailed description which follows and will be otherwise apparent to those skilled in the art. For purposes of illustration of this invention, a preferred embodiment is shown and described herein below in the accompanying drawing. It is to be understood that this is for the purpose of example only and that the invention is not limited thereto.

IN THE DRAWINGS

DESCRIPTION OF THE INVENTION

Figure 1:
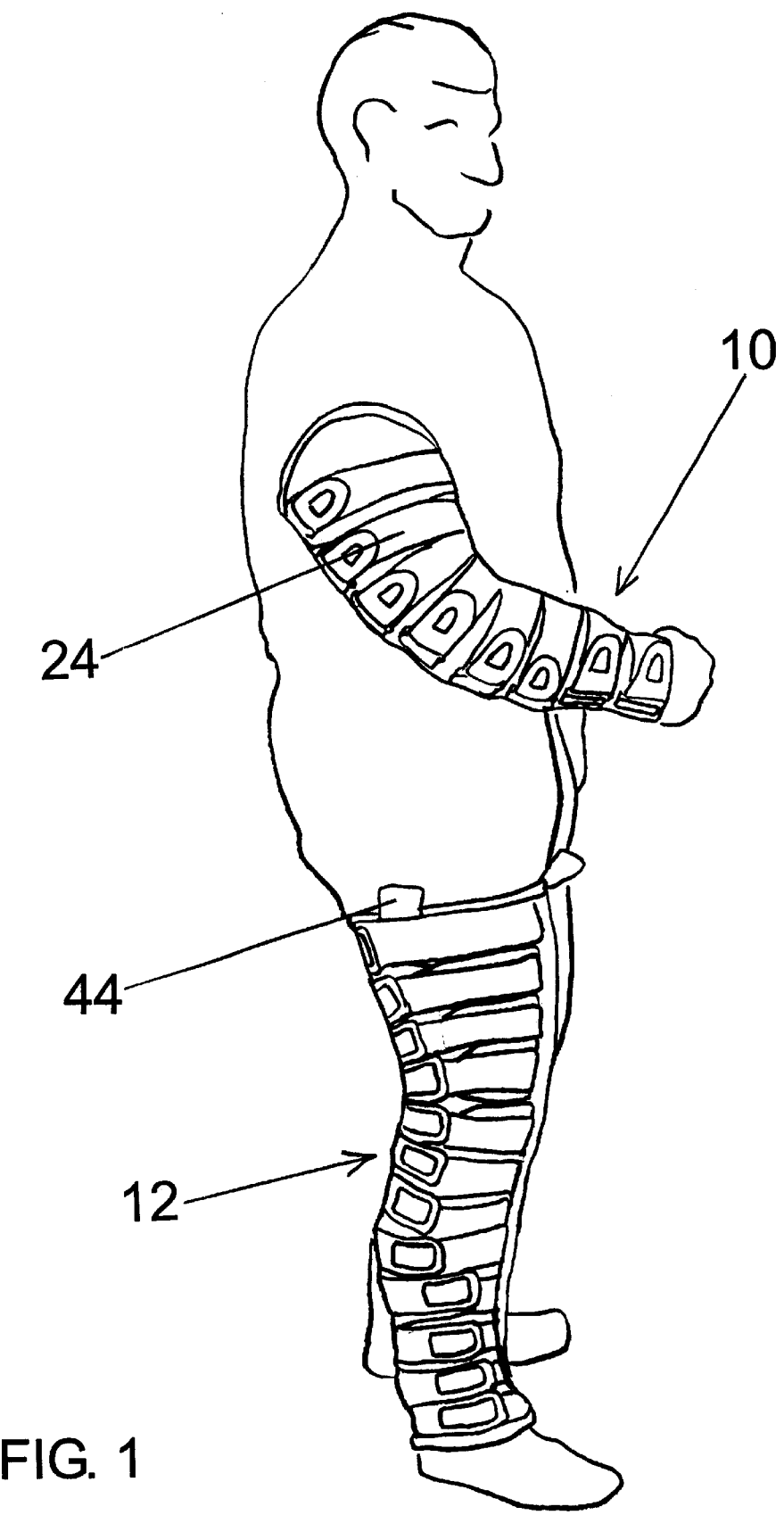
FIG. 1 is a perspective view of a person wearing compression sleeves of the instant invention, one configured to fit over the arm and the other configured to fit over the leg.
Figure 2:
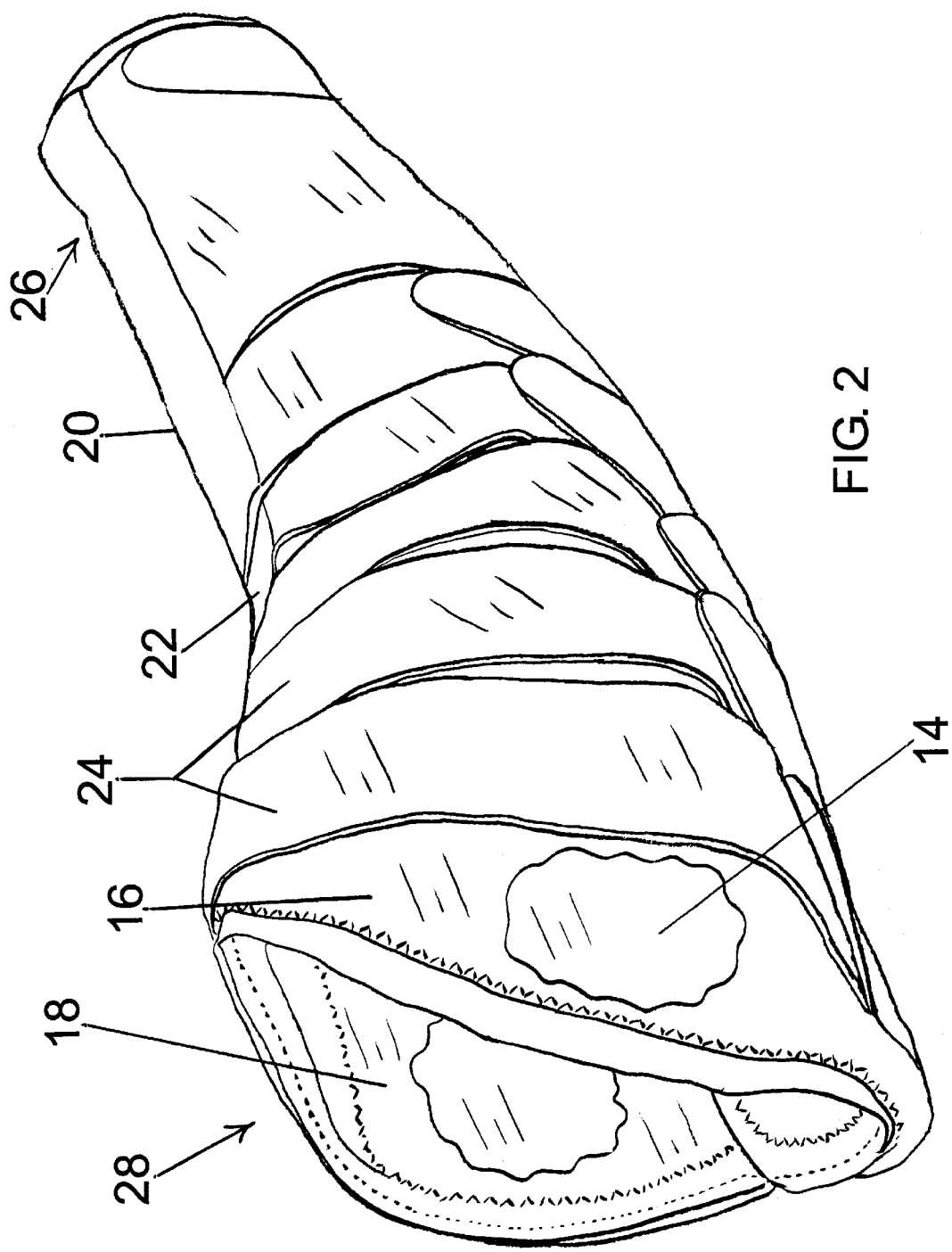
FIG. 2 is a perspective view of the compression sleeve with various elements being removed or partially broken away.

The invention comprises a sleeve designed to fit over a patient's limb as shown in FIG. 1. Embodiments of the sleeve include one which is adapted to fit over an arm, identified generally by the reference numeral 10, and one which is designed to fit over the leg, identified generally by the reference numeral 12. Each sleeve is comprised of an inner flexible sheet padding layer 14 and an outer fabric layer 16 as shown in FIG. 2. Portions of the sleeve components are partially removed for a better view of the inner padding layer. The outer fabric layer 16 must be comprised of an inelastic material, such as a non-woven micro-fiber, to provide static compression to constrain the swelling of the limb. An inner mesh fabric layer 18 may be sewn onto an interior side of outer fabric layer 16 to form a pocket for supporting inner padding layer 14. Optionally, inner padding layer 14 may itself be affixed to outer fabric layer 16 by sewing or the like. One configuration of the padding is such that there is a gap between opposing longitudinal edges of the padding within the sleeve. This allows for the edges of the padding to overlap during compression for a snug fit over the limb. The layer materials should be air permeable to reduce the generation of body heat within the sleeve. The sleeve forms an elongated, tubular-shaped member 20 for receiving a patent's limb. It has a tapered configuration to conform to the general contour of the limb. Outer fabric layer 16 may be sewn and assembled together such that a slight bend 22 is formed at the general proximity of a patient's elbow to approximate the angular disposition of the arm in a normal resting position. Thus the arm sleeve can be constructed to have an angular aspect of about 160 to 175 degrees of the distal end in relation to the proximal end.

Figure 8:
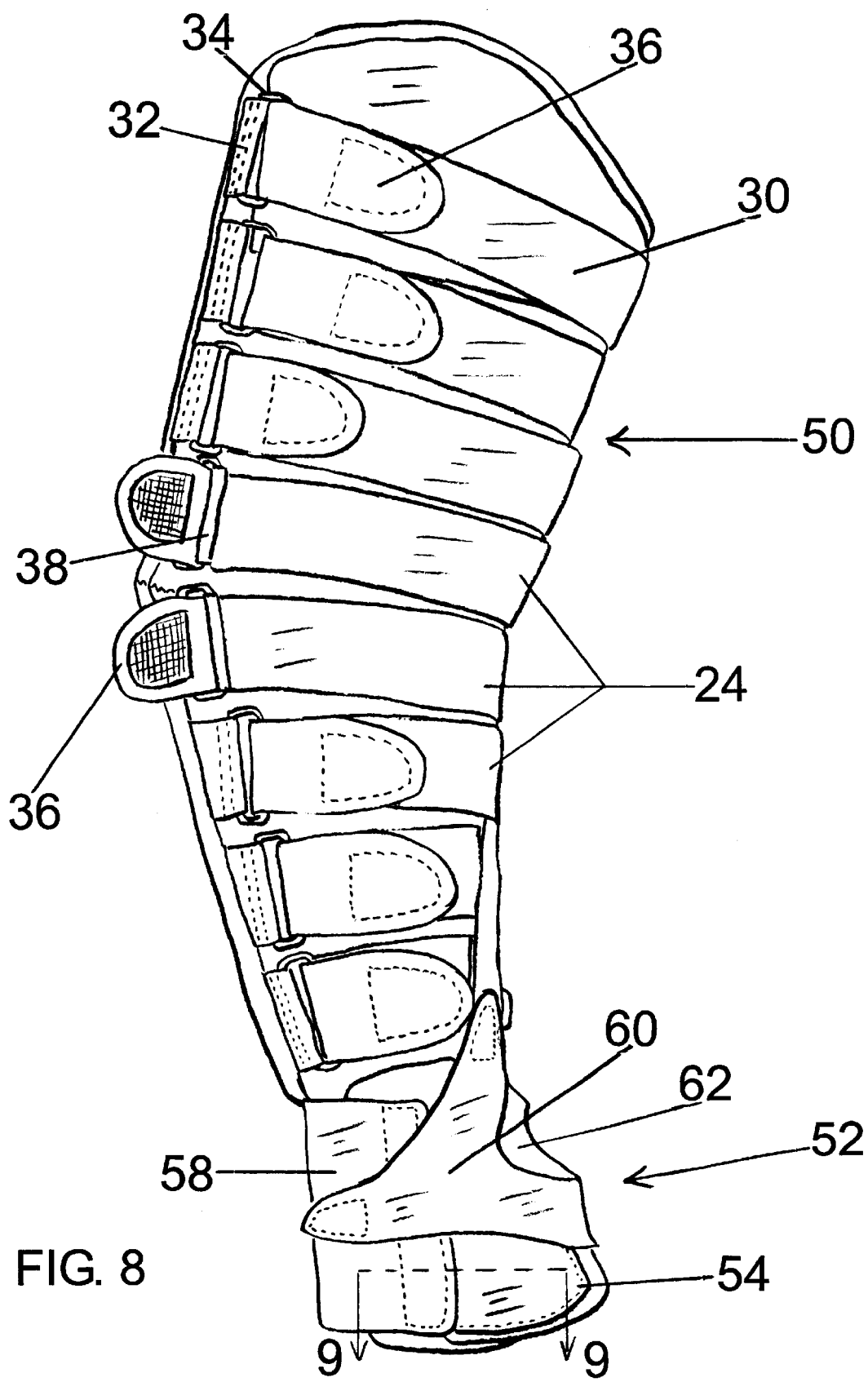
FIG. 8 is a view in side elevation of another embodiment of the compression sleeve configured to fit over the arm.
Figure 9:
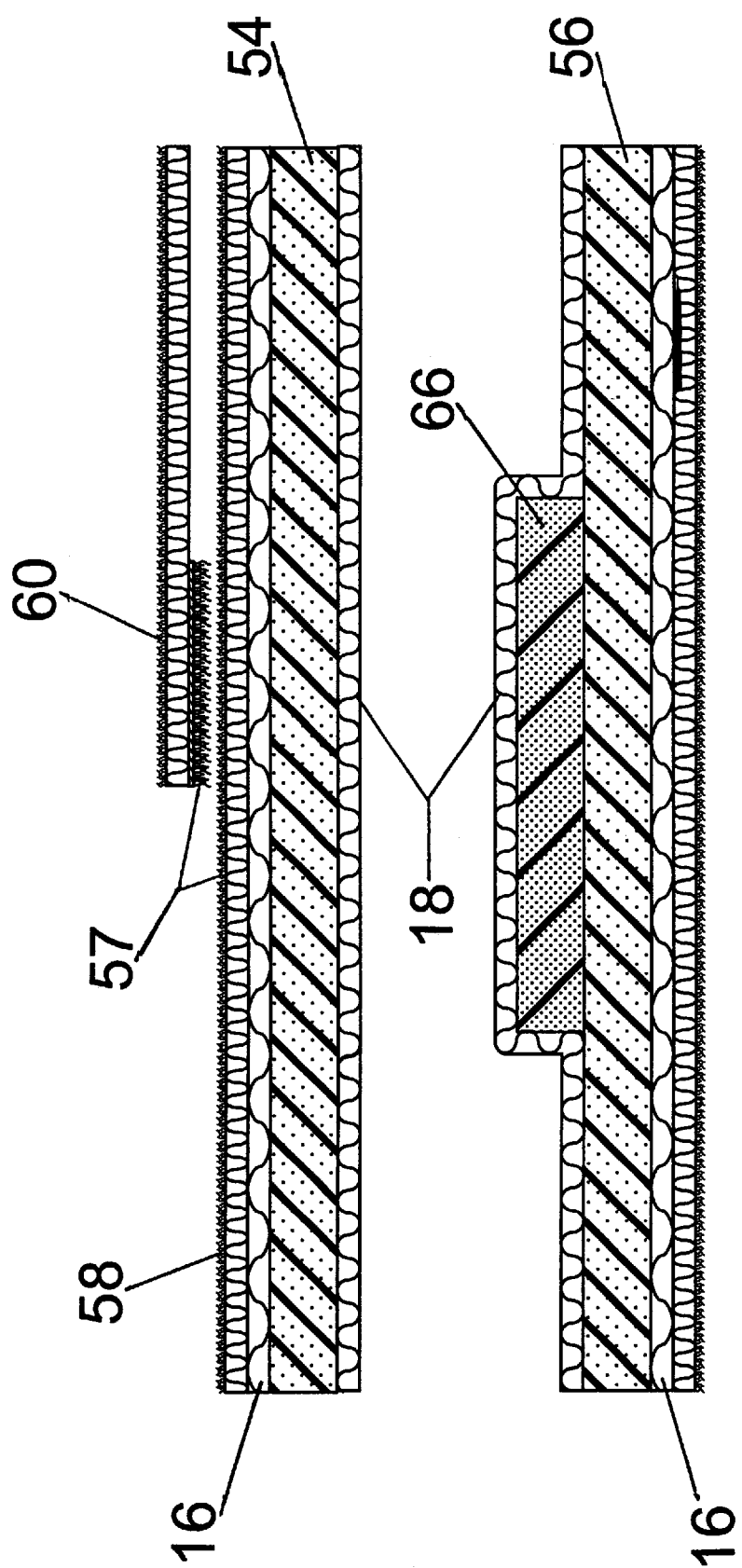
FIG. 9 is a cross-sectional view taken along the lines 9—9 of FIG. 8.

A plurality of tightening straps 24 for applying circumferential pressure are disposed about the sleeve and are placed laterally in vertical succession along sleeve 20. Each individual strap can be tightened independently of the other straps such that a fixed, gradient compressive pressure along the length of the sleeve is capable of being effected. With this arrangement, straps located at a distal end 26 of the sleeve can be tightened to a greater degree than the straps at a proximal end 28 of the sleeve so that the gradient compression along the limb can be achieved. This independent tightening of the straps thus facilitates the directional massaging of the lymph out of the limb. Straps 24 are disposed in close adjacent proximity to each other so that the compression gradient is not disrupted and also to minimize the potential for pockets of swelling from bulging out from beneath and between the straps. Such a condition, called windowing, could lead to trapped pools of lymph which would remain in the limb. As shown in FIG. 8, straps 24 each comprise an elongated strap member 30 having one end affixed to outer fabric layer 16. A corresponding D-ring strap member 32 is provided at a distance spaced laterally apart from the connection point of strap 30. D-ring strap member 32 comprises a D-ring 34 through which a free end 36 of strap 30 is passed. Complementary hook and loop fastening material, such as Velcro®, is provided on strap end 36 and on the surface of strap 30 for securing the strap upon tightening. Roller bearings 38 are provided on D-rings 34 to create a pulley effect to aid in tightening the straps. As it can be appreciated, a patient may experience difficulty in tightening a strap around a padded sleeve and the roller bearings enable the patient to pull the straps with greater force to achieve the necessary degree of compression.

Figure 3:
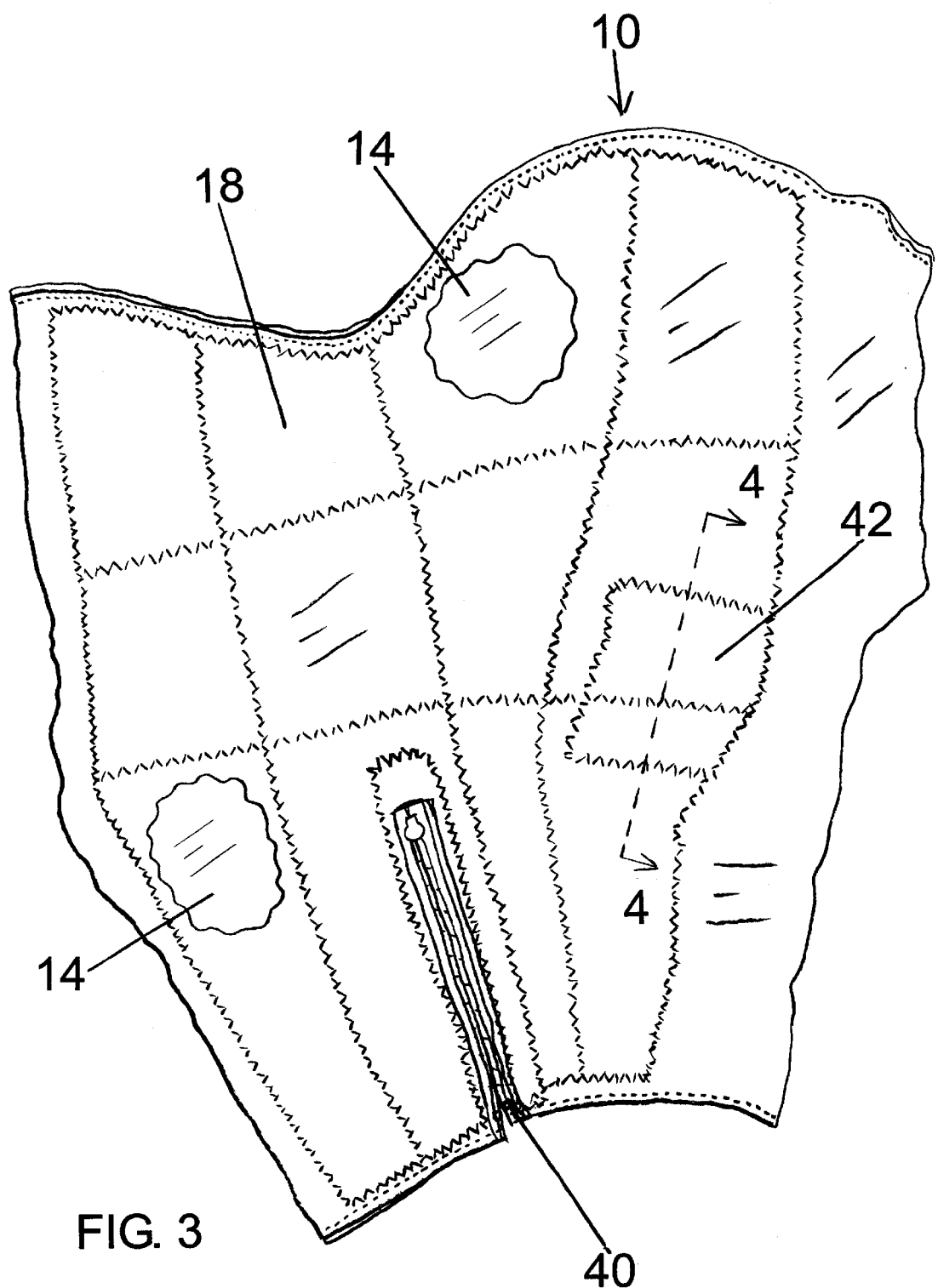
FIG. 3 is a laid-open view of the compression sleeve configured for use with the arm showing various elements partially broken away.
Figure 4:
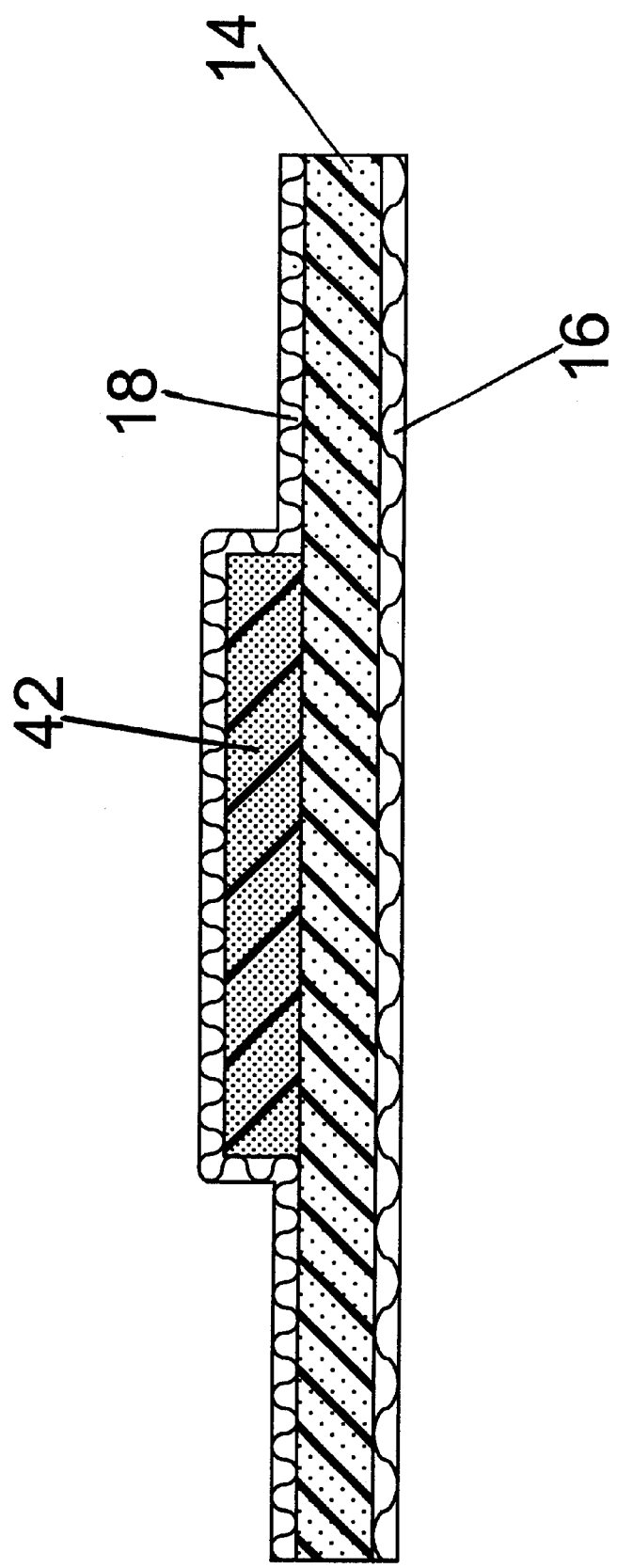
FIG. 4 is a cross-sectional view taken along the lines 4—4 of FIG. 3 showing the various layers of the compression sleeve.

FIG. 3 shows arm sleeve 10 split open and laid flat to show its various inner components. Portions of the sleeve components are partially removed for a better view of the inner padding layer. Inner padding layer 14 is shown held in place by inner fabric material 18. This fabric may be comprised of a lightweight nylon mesh material. As the overall shape of the sleeve is somewhat tapered, a zipper 40 is disposed within the end of the sleeve to facilitate donning by the user. Prior to wearing, zipper 40 can be unzipped so the distal end of the sleeve can be opened to accommodate the patient's hand. Certain areas within the sleeve may be provided with supplemental padding 42, such as the elbow area, to provide comfort to the patient from stress points caused by bending of the arm within the sleeve. The density and firmness of padding 42 may be varied depending on the level of support desired. FIG. 4 provides a cross-sectional view of the sleeve showing the padding and fabric layers.

Inner padding layer 14 is comprised of a high density foam, such as polyurethane foam, preferably in the range between 2.2 to 6.0 pounds per cubic foot. This foam padding is thin, preferably about ¼ inch thick. It has a flat, even surface with no raised projections. This padding layer should have adequate firmness, and should possess sufficient compressibility qualities to withstand the pressure generated by tightening straps 24 so that a general, even pressure placed on the inner padding layer can be imparted to the patient's limb. A suitable type of such foam padding is that manufactured by Lohmann GmbH and Co., KG, and sold under the trademark KOMPREX®. The foam padding's firmness qualities can be expressed as a function of how it can support a force at different compression levels. Typically, to measure such firmness, the ratio (compression modules) of the compressive force needed to indent the foam to 25% and 50%, respectively, of its thickness is determined. The greater the value of this ratio, the greater the degree of firmness that is offered by the foam. Low density foams have a compression modulus of around 1.20, which offers very little firmness. To adequately distribute the compressive force generated by the tightening straps around the sleeve, the inner padding layer 14 should be comprised of a foam having a compression modulus of 2.0 or greater.

Figure 5:
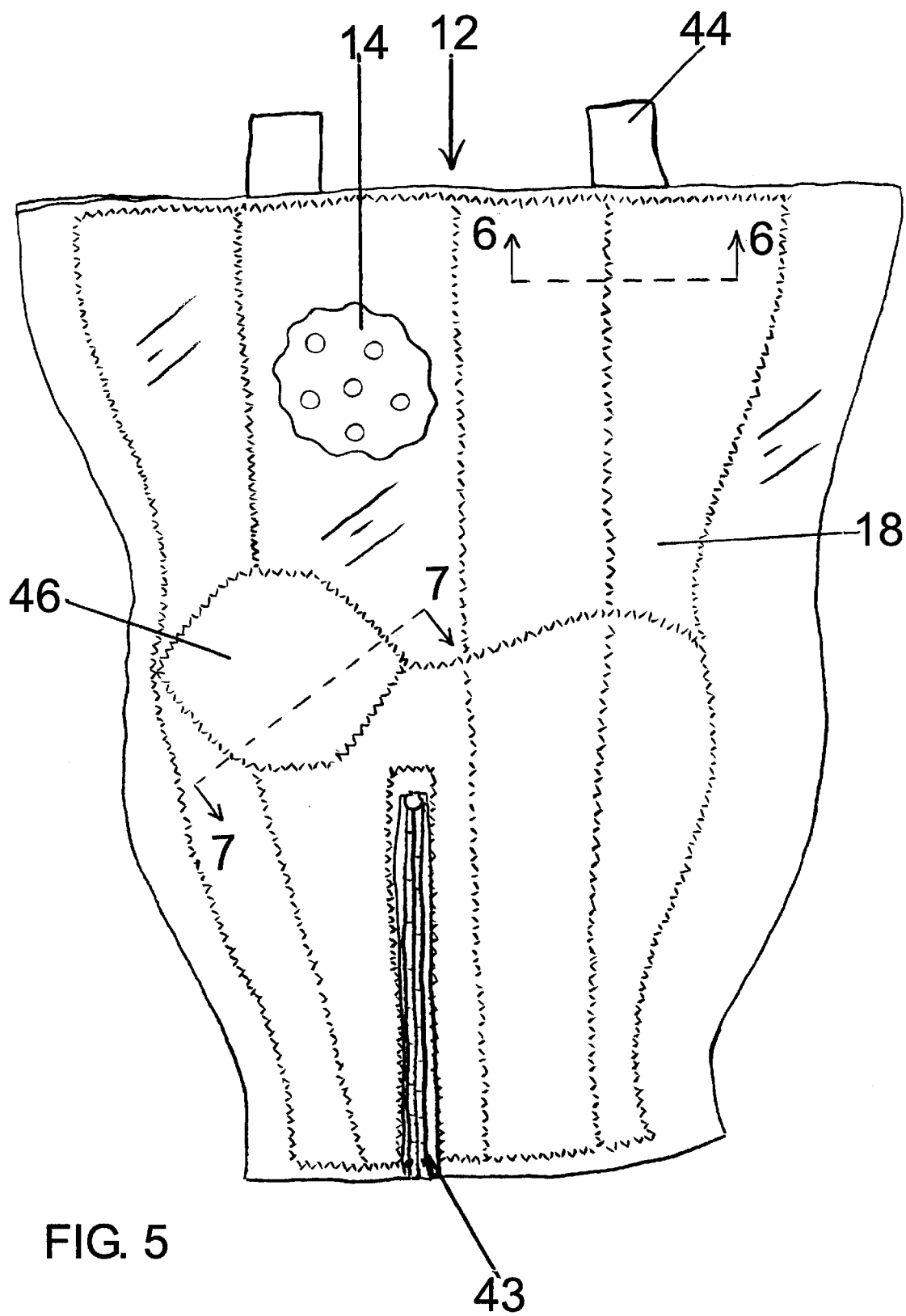
FIG. 5 is a laid-open view of the compression sleeve configured to fit over the leg showing various materials partially broken away.
Figure 6:
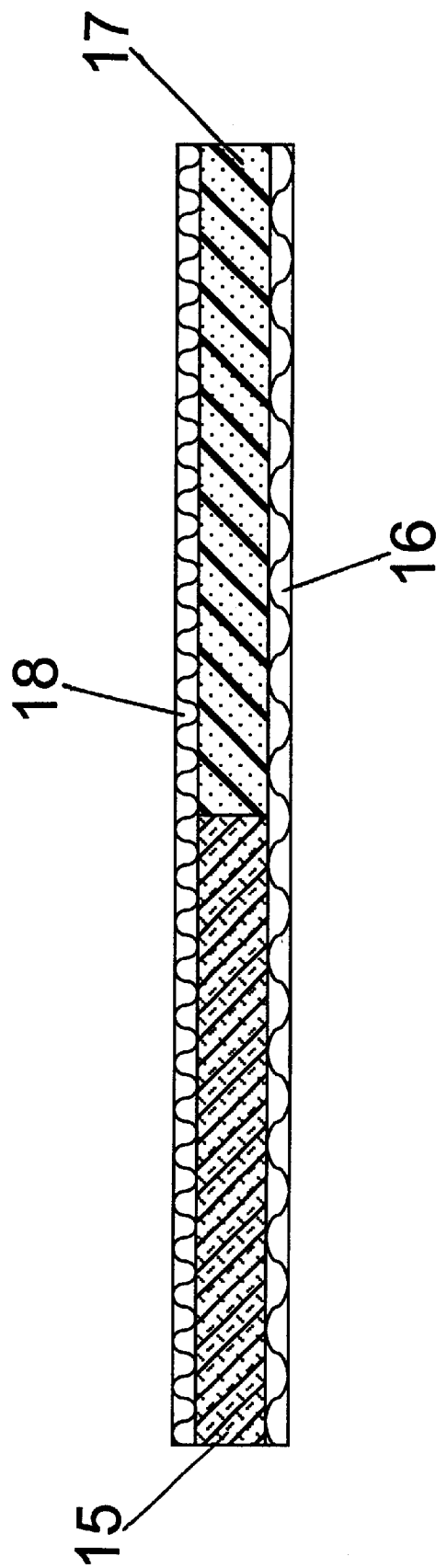
FIG. 6 is a cross-sectional view taken along lines 6—6 of FIG. 5.
Figure 7:
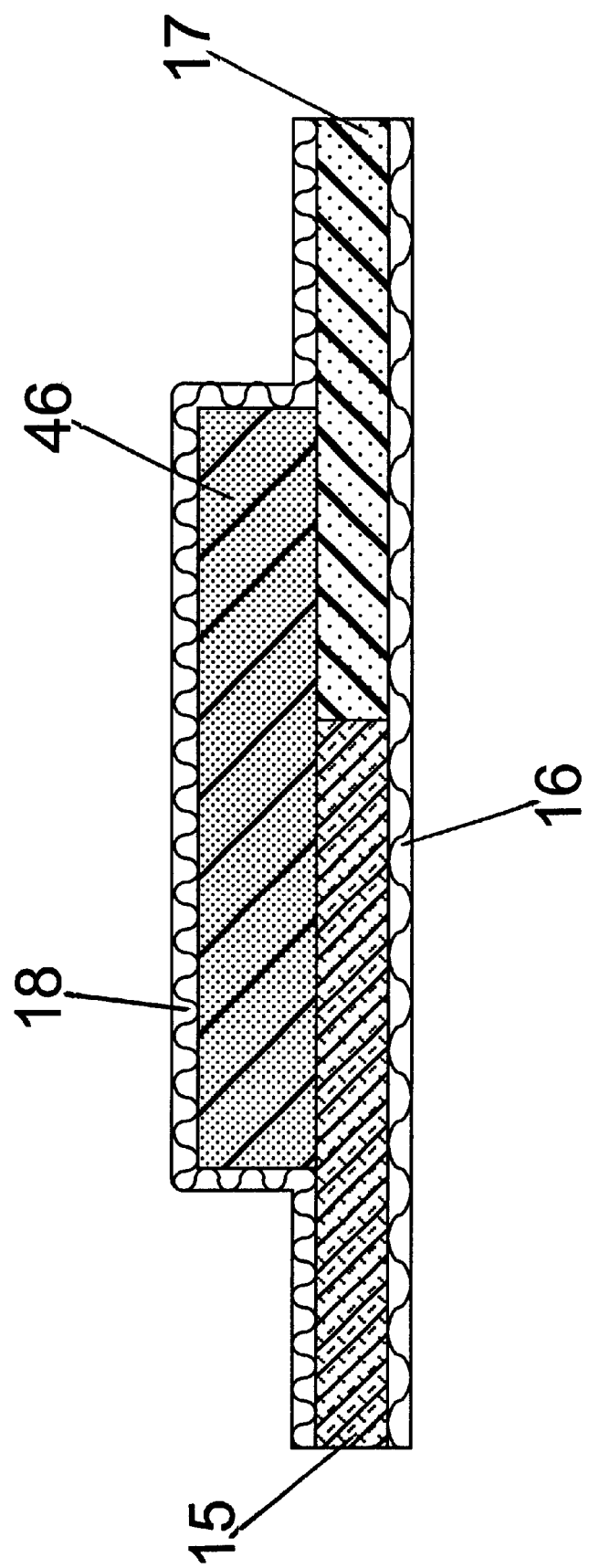
FIG. 7 is a cross-sectional view taken along lines 7—7 of FIG. 5.

FIG. 5 shows leg sleeve 12 laid open flat to show its component parts. As the leg sleeve comprises an amount of padding material sufficient to cover the entire length of the limb, the weight of the sleeve can become somewhat heavy. Accordingly, it may become difficult at times to maintain the sleeve in place on a patient's leg if the patient is ambulatory during treatment with the sleeve. To minimize the downward migration of the sleeve due to its weight, the inner padding 14 of the leg sleeve 12 may be comprised of two pad components 15 and 17 of differing density bonded or sewn together as can be seen in FIGS. 6 and 7. The lower density foam will be of lighter weight thus helping to alleviate the downward migration of the sleeve. As an example, for the leg sleeve, the higher density portion of the padding may be comprised of the VOLARA® foam, and the lower density portion may be comprised of the KOMPREX® foam. As another means to prevent migration, the secondary foam material may have a higher degree of rigidity to maintain the elongated sleeve shape, while the primary foam material may be more flexible to more easily wrap around the contour of the leg. Tabs 44 may be provided at the top of the sleeve for the patient to grasp whereby the sleeve can be pulled up if it slips down the leg. Additional internal padding 46 may be provided at certain areas such as the knee to provide comfort to the patient from stress points caused by bending the knee. Zipper 43 is provided at the lower end of the sleeve, which can be opened prior to donning so that the sleeve may be passed over the foot and ankle.

The inner padding 14 of either sleeve may be provided with a plurality of apertures as shown in FIG. 5. These apertures further help to decrease the weight of the pad, by cutting down on the amount of material, and also provide a means for keeping the patient's skin cool as it helps to release trapped heat from the sleeve. The apertures optimally have a ¼ inch diameter; a sufficient number of such apertures can be provided in the padding such that up to 20% reduction in the amount of padding can be achieved.

As an alternate type of inner padding, a gel sheet may be used such as that manufactured by Action Products, Inc. and sold under the trademark AKTON®. Gel sheets are a viscoelastic polymer which have a good compressibility quality that helps to evenly distribute the pressure generated by the compression straps. Gel sheets also have a high heat flux capacity that helps to keep the patient's limb cool by drawing off excess heat. To increase the breathability of the gel sheet and allow air to pass in and out of the sleeve, holes may be provided in the gel sheet.

An alternate embodiment of the arm sleeve is shown in FIG. 8 and is generally indicated by the reference numeral 50. It comprises the general configuration of the arm sleeve but further includes a glove member 52. Glove member 52 comprises opposing pad elements 54 and 56 which are disposed to receive a patient's palm therebetween. Elastic straps 58 and 60 are used to draw the pads tight around the patient's hand. A gap 62 is provided in strap 60 through which a patient's thumb can extend. Hook and loop fastening material 57 is provided on straps 58 and 60 and on pads 54 and 56 so that glove member 52 may be drawn tightly around the patient's hand. Outer inelastic layer 16, inner padding layer 14 and inner fabric layer 18 extend continuously from the sleeve over glove member 52. Inner padding layer splits off to form pads 54 and 56. A supplemental pad 66 of higher density may be placed in the palm region for user comfort and so that a substrate against which compression can be generated is provided.

Various changes and modifications may be made within this invention as will be apparent to those skilled in the art. Such changes in modifications are within the scope and teaching of this invention as defined in the claims appended hereto.

What is claimed is:

1. A compression sleeve for applying pressure to a person's limb, said sleeve comprising:

an inner flexible sheet padding layer,
an outer inelastic fabric layer, and
a plurality of tightening straps,
said outer inelastic fabric layer providing a source of static compression, said tightening straps being disposed laterally in vertical succession along an exterior side of said sleeve to apply circumferential pressure along a length of said sleeve, said inner padding layer comprising a high density foam material in a thin, continuous surface flat sheet.

2. The compression sleeve of claim 1 in which said tightening straps are capable of being tightened independently of each other, whereby a gradient compressive pressure along said length of said sleeve is capable of being effected.

3. The compression sleeve of claim 2 in which each of said tightening straps comprises a strap member having a first end connected to said outer layer of said sleeve and a second free end, a D-ring member being provided on said sleeve at a distance spaced apart from said first end of said strap member, said second end of said strap member being adapted to pass through and be drawn tight against said D-ring, means being provided for securing said second end of said strap member, said D-ring member having a roller bearing.

4. The compression sleeve of claim 1 in which said tightening straps are disposed in substantially adjacent proximity to each other along said sleeve to minimize space between said straps to prevent a bulging out of said sleeve between said straps.

5. The compression sleeve of claim 1 in which an interior fabric liner is connected to said outer layer to form a pocket therebetween, said inner padding layer being positioned within said pocket.

6. The compression sleeve of claim 5 in which a gap exists between longitudinal edges of said inner padding layer, said edges being capable of being overlapped upon each other upon compression of said sleeve.

7. The compression sleeve of claim 5 in which said fabric liner is comprised of a lightweight mesh material.

8. The compression sleeve of claim 1 in which said inner padding layer has a plurality of apertures disposed therein, said apertures each having a diameter of approximately ¼ inch, said apertures comprising around 20% of the area of said inner padding layer.

9. The compression sleeve of claim 1 in which said inner padding layer has a density in a range of between of 2.2 to 6.0 pounds per cubic foot.

10. The compression sleeve of claim 1 in which said inner padding layer has a compression modulus of 2.0 or greater.

11. The compression sleeve of claim 1 in which a zipper is provided at a distal end of said sleeve to allow said distal end of said sleeve to be widened prior to donning over a limb of a person.

12. The compression sleeve of claim 11 having a tapered shape, decreasing in circumference from a proximal end to said distal end.

13. The compression sleeve of claim 1 in which said tightening straps are capable of being tightened independently of each other, whereby a gradient compressive pressure along said length of said sleeve is capable of being effected, each of said tightening straps comprises a strap member having a first end connected to said outer layer of said sleeve and a second free end, a D-ring member being provided on said sleeve at a distance spaced apart from said first end of said strap member, said second end of said strap member being adapted to pass through and be drawn tight against said D-ring, means being provided for securing said second end of said strap member, said tightening straps being disposed in close adjacent proximity to each other along said sleeve to minimize a bulging out of said inner layer between said straps, a fabric liner being connected to said outer layer to form a pocket therebetween, said inner padding layer being positioned within said pocket, a zipper being provided at a distal end of said sleeve to allow said distal end of said sleeve to be widened prior to donning over a limb of a person.

14. The compression sleeve of claim 1 in which said sleeve is configured to fit over a person's arm, a distal end of said sleeve having attached thereto a hand receiving member for applying compressive pressure to opposing planar surfaces of said person's hand.

15. The compression sleeve of claim 13 in which said hand receiving member is comprised of a pair of opposing pad members, straps being provided to draw said pad members in compressive engagement with said hand.

16. The compression sleeve of claim 1 in which said sleeve is configured to fit over a person's arm, said sleeve forming an angle from a proximal end to a distal end of about 160 to 175°.

17. The compression sleeve of claim 1 in which said sleeve is configured to fit over a person's arm, a supplemental pad being disposed within said sleeve at a position approximating a location of an elbow of said person's arm.

18. The compression sleeve of claim 1 in which said sleeve is configured to fit over a person's leg, said inner padding layer comprising a thin, continuous surface flat sheet formed of a first and second high density foam material connected adjacently and co-planar with each other, said second foam material having a lower density than said first foam material.

19. The compression sleeve of claim 18 in which pull tab members are provided at a proximal end of said sleeve, said pull tab members providing means by which a person wearing said sleeve can draw said sleeve up said person's leg.

20. The compression sleeve of claim 18 in which a low density foam pad is disposed at a position on an interior side of said sleeve approximating a location of a person's knee.

21. The compression sleeve of claim 20 in which said foam pad has a density of less than 2.0 pounds per cubic foot.

22. The compression sleeve of claim 16 in which said tightening straps are capable of being tightened independently of each other, whereby a gradient compressive pressure along said length of said sleeve is capable of being effected, each of said tightening straps comprises a strap member having a first end connected to said outer layer of said sleeve and a second free end, a D-ring member being provided on said sleeve at a distance spaced apart from said first end of said strap member, said second end of said strap member being adapted to pass through and be drawn tight against said D-ring, means being provided for securing said second end of said strap member, said tightening straps being disposed in close adjacent proximity to each other along said sleeve to minimize a bulging out of said inner layer between said straps, a fabric liner being connected to said outer layer to form a pocket therebetween, said inner padding layer being positioned within said pocket, a zipper being provided at a distal end of said sleeve to allow said distal end of said sleeve to be widened prior to donning over a limb of a person, a supplemental pad being disposed within said sleeve at a position approximating a location of an elbow of said person's arm.

23. The compression sleeve of claim 18 in which said tightening straps are capable of being tightened independently of each other, whereby a gradient compressive pressure along said length of said sleeve is capable of being effected, each of said tightening straps comprises a strap member having a first end connected to said outer layer of said sleeve and a second free end, a D-ring member being provided on said sleeve at a distance spaced apart from said first end of said strap member, said second end of said strap member being adapted to pass through and be drawn tight against said D-ring, means being provided for securing said second end of said strap member, said tightening straps being disposed in close adjacent proximity to each other along said sleeve to minimize a bulging out of said inner layer between said straps, a fabric liner being connected to said outer layer to form a pocket therebetween, said inner padding layer being positioned within said pocket, a zipper being provided at a distal end of said sleeve to allow said distal end of said sleeve to be widened prior to donning over a limb of a person, a supplemental pad being disposed within said sleeve at a position approximating a location of a person's knee.

24. A compression sleeve for applying pressure to a person's limb, said sleeve comprising:
   an inner flexible sheet padding layer,
   an outer inelastic fabric layer, and
   a plurality of tightening straps,
   said inner and outer layers each having an area dimension being substantially co-extensive with each other, said outer inelastic fabric layer providing a source of static compression, said tightening straps being disposed laterally in vertical succession along an exterior side of said sleeve to apply circumferential pressure along a length of said sleeve, said inner padding layer comprising a gel material in a thin, continuous surface flat sheet.

25. The compression sleeve of claim 24 in which said tightening straps are capable of being tightened independently of each other, whereby a gradient compressive pressure along said length of said sleeve is capable of being effected.

26. The compression sleeve of claim 25 in which each of said tightening straps comprises a strap member having a first end connected to said outer layer of said sleeve and a second free end, a D-ring member being provided on said sleeve at a distance spaced apart from said first end of said strap member, said second end of said strap member being adapted to pass through and be drawn tight against said D-ring, means being provided for securing said second end of said strap member, said D-ring member having a roller bearing.

27. The compression sleeve of claim 24 in which said tightening straps are disposed in substantially adjacent proximity to each other along said sleeve to minimize space between said straps to prevent a bulging out of said sleeve between said straps.

28. The compression sleeve of claim 24 in which an interior fabric liner is connected to said outer layer to form a pocket therebetween, said inner padding layer being positioned within said pocket.

29. The compression sleeve of claim 28 in which said fabric liner is comprised of a lightweight mesh material.

30. The compression sleeve of claim 24 in which a zipper is provided at a distal end of said sleeve to allow said distal end of said sleeve to be widened prior to donning over a limb of a person.

31. The compression sleeve of claim 30 having a tapered shape, decreasing in circumference from a proximal end to said distal end.

32. The compression sleeve of claim 23 in which said tightening straps are capable of being tightened independently of each other, whereby a gradient compressive pressure along said length of said sleeve is capable of being effected, each of said tightening straps comprises a strap member having a first end connected to said outer layer of said sleeve and a second free end, a D-ring member being provided on said sleeve at a distance spaced apart from said first end of said strap member, said second end of said strap member being adapted to pass through and be drawn tight against said D-ring, means being provided for securing said second end of said strap member, said tightening straps being disposed in close adjacent proximity to each other along said sleeve to minimize a bulging out of said inner layer between said straps, a fabric liner being connected to said outer layer to form a pocket therebetween, said inner padding layer being positioned within said pocket, a zipper being provided at a distal end of said sleeve to allow said distal end of said sleeve to be widened prior to donning over a limb of a person.

33. The compression sleeve of claim 24 in which said sleeve is configured to fit over a person's arm, said sleeve forming an angle from a proximal end to a distal end of about 160 to 175°.

34. The compression sleeve of claim 24 in which said sleeve is configured to fit over a person's arm, a distal end of said sleeve having attached thereto a hand receiving member for applying compressive pressure to opposing planar surfaces of said person's hand.

35. The compression sleeve of claim 34 in which said hand receiving member is comprised of a pair of opposing pad members, straps being provided to draw said pad members in compressive engagement with said hand.

36. The compression sleeve of claim 24 in which said sleeve is configured to fit over a person's arm, a supplemental pad being disposed within said sleeve at a position approximating a location of an elbow of said person's arm.

37. The compression sleeve of claim 24 in which said sleeve is configured to fit over a person's leg, pull tab members being provided at a proximal end of said sleeve, said pull tab members providing means by which a person wearing said sleeve can draw said sleeve over said person's leg.

* * * * *